United States Patent [19]

Sandstrom

[11] 4,167,946
[45] Sep. 18, 1979

[54] MEDICAL AID FOR INSERTION OF INSTRUMENTS THROUGH THE MOUTH

[75] Inventor: Anne M. Sandstrom, Sodertalje, Sweden

[73] Assignee: Kemi-Intressen AB, Sundbyberg, Sweden

[21] Appl. No.: 818,258

[22] Filed: Jul. 22, 1977

[30] Foreign Application Priority Data

Jul. 23, 1976 [SE] Sweden .................................. 7608426

[51] Int. Cl.² ........................................... A61M 25/02
[52] U.S. Cl. ..................................... 128/351; 128/12; 128/208; 128/DIG. 26
[58] Field of Search ..................... 128/12–15, 128/208, 348–351, 133, 136, DIG. 26; 138/103; 174/47

[56] References Cited

U.S. PATENT DOCUMENTS

| 2,908,269 | 10/1959 | Cheng | 128/12 |
| 2,981,254 | 4/1961 | Vanderbilt | 128/350 R |
| 3,722,508 | 3/1973 | Roberts | 128/133 |
| 3,760,811 | 9/1973 | Andrew | 128/351 |
| 3,825,004 | 7/1974 | Durden | 128/275.1 |
| 3,946,742 | 3/1976 | Eross | 128/351 |
| 3,961,647 | 6/1976 | Doubleday | 174/47 X |

*Primary Examiner*—Dalton L. Truluck
*Attorney, Agent, or Firm*—Fred Philpitt

[57] ABSTRACT

A device for protecting both a patient's teeth and medical instruments (such as tubes, probes, etc.) against damage when such instruments are inserted through the mouth. The device comprises a teeth shield member of semi-rigid material with dimensions greater than the instrument introduced and a support member for the instrument at the periphery of the teeth shield member for securing a side-by-side relationship between the instrument and the teeth shield member. The support member can be in the shape of a slit-open tube into which the instrument can be inserted radially after the introduction of the instrument into the patient. The instrument can be fixed by means of a band tied around the instrument and tied or otherwise fixed to the device, which band can also be used to fix the complete unit in the patient by tieing around his neck.

11 Claims, 9 Drawing Figures

MEDICAL AID FOR INSERTION OF INSTRUMENTS THROUGH THE MOUTH

BACKGROUND

In many medical situations, when an instrument is to be inserted into a patient's throat through his mouth, there is a need to protect both the inserted instrument and the teeth of the patient against damage by biting action. There is also a need to secure the inserted instrument so as to prevent it from excessive movement in the mouth-cavity which could both adversely affect the function of the instrument and cause damage to the patient. These needs are of special significance when the patient cannot control his movements, for example under narcosis, and when a reliable functioning of the inserted instrument is essential. Thus, it has been a general rule that some kind of teeth-shield of semi-rigid material should be placed between the patient's teeth during operations when a tube (e.g. an endotracheal tube) is inserted down the trachea of the patient and through which the patient is provided with oxygen or anaesthetic gas.

Heretofore rolls of textile fabric or pieces of tubing of suitable dimensions have been used as teeth-shields. The main problem with these types of teeth-shields has been the difficulty in rigidly fixing the instrument adjacent to the teeth-shield and also in fixing this unit rigidly in the mouth of the patient so that the unit is prevented from performing rotational movements or movement either out of the mouth-cavity or deeper down into the throat. This fixing must be achieved to make it possible for the teeth-shield to perform its purposes of offering resistance to biting before the instrument comes into contact with the teeth and to guarantee a proper positioning of the instrument for correct functioning in the patient. In an effort to achieve fixation of the shield and the instrument sticking-plaster or special tapes have been used. In this way enough friction has usually been obtained to hold together an instrument and a teeth-shield. However, the sticking-plaster or tape has had the disadvantage that it becomes soaked with saliva or blood and often adheres to the patient's hair or beard or even to the skin. A teeth-shield in the shape of a roll has had the added disadvantage of providing very little space for insertion of additional instruments through the mouth.

German Offenlegungsschrift No. 2,120,164 proposes arranging a body of soft material around a tube to be inserted into the mouth and to give this body such a size as to prevent it from penetrating too deeply into the mouth. This device is, however, not generally usable since the opening through the body must be varied in size in accordance with the size of each tube or group of tubes that are to be used in order to prevent free movement. As a consequence of its size and because the tubing completely fills up the opening, this device doesn't provide any space for the insertion of additional instruments and also cannot be maintained at a fixed location in the mouth-cavity.

The object with the present invention is to provide a device for insertion of instruments, such as tubes, probes, etc., through the mouth of a patient by aid of which the above discussed problems are reduced or eliminated.

THE PRESENT INVENTION

Considered from one aspect, my invention involves a device for protecting a medical instrument that is to be inserted through the mouth of a patient, said device comprising in combination (a) a tubular teeth shield member having a maximum internal diameter that is greater than the external diameter of said medical instrument, and (b) an instrument support member fixed to and extending along the exterior side of said tubular teeth shield member in a direction generally parallel to the longitudinal axis of said tubular teeth shield member, said instrument support member having a generally U-shaped configuration that opens outwardly so that it can receive and hold a medical instrument.

The invention will be better understood by reference to the following detailed description when read in conjunction with the drawings wherein FIGS. 1 and 2 are perspective views of one embodiment of my invention;

In all of the drawings the tubular teeth shield member 2 is seen to be in the form of a generally cylindrical hollow tube. The instrument support member 3 in each instance is fixed to and extends along the exterior side of said tubular teeth shield member 2 in a direction that is generally parallel to the longitudinal axis of the tubular teeth shield member 2. The instrument support member 3 preferably has a generally U-shaped configuration. Most preferably the instrument support member 3 is in the form of a slotted cylindrical section that merges into or through the wall of said teeth shield member 2.

Figure 1:
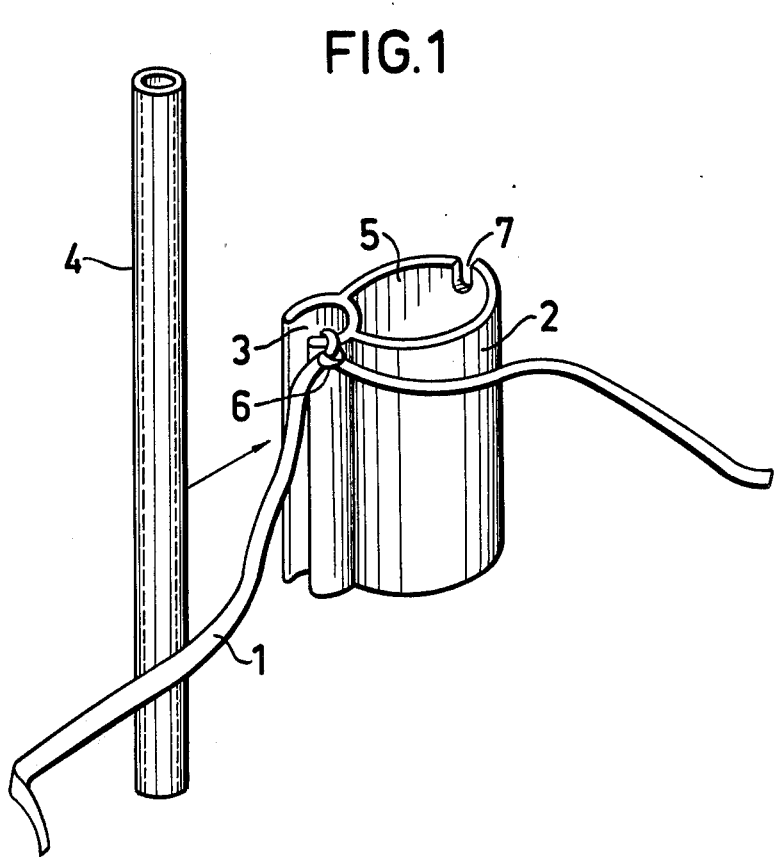
Figure 2:
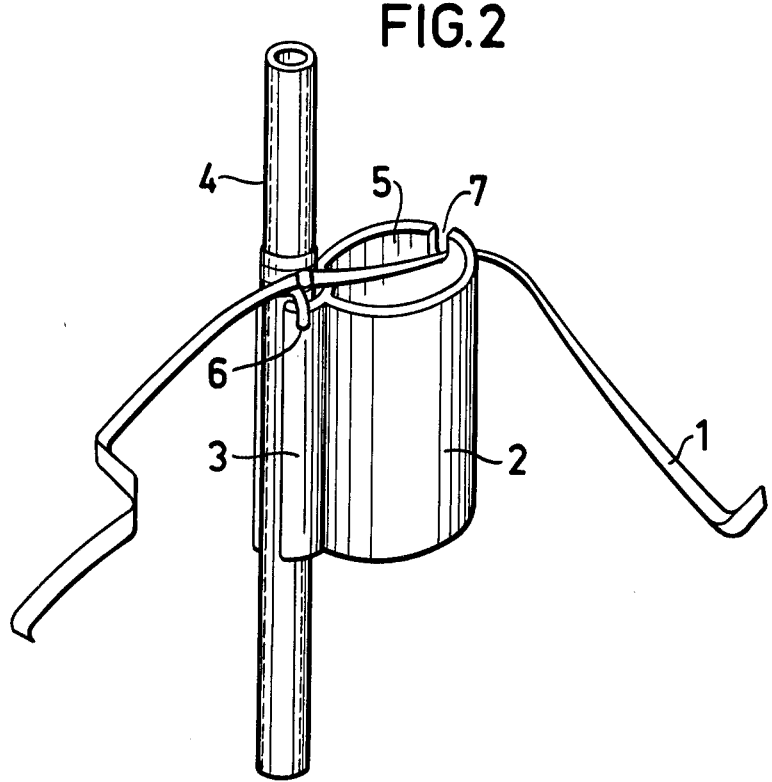

The medical instrument is shown as 4 in the drawings. This instrument could be a tube, or a probe, or any other piece of medical equipment that might be inserted through the mouth and down into the throat of a patient. As indicated by the arrow in FIG. 1, the slit in support member 3 allows the tube 4 to be inserted radially into the support 3, which means that the entire device can be put together after the tube 4 has been inserted into the throat of a patient. This is an important feature since an already attached teeth-shield would interfere with the insertion of the instrument, especially since in many cases additional instruments are needed at the time of insertion. The slit also has the advantage that the support member 3 is flexible enough to adapt itself to instruments of different shape and diameter. When the support member 3 is tube-shaped, as shown, the contact surface against the tube 4 is large, which means that the tube can be rather readily held in place by means of simple tieing. The length of the support-tube 3 also contributes to an effective securing of the tube 4 parallel to the longitudinal axis of the teeth-shield member 2. Also, whereas the support-tube 3 securely holds the tube 4, it is still possible to insert additional instruments through the cavity 5 of tubular member 2. This design is preferred since the insertion of extra instruments through the cavity 5 can be done without hindrance to or adverse effects upon the tube 4.

Figure 3:
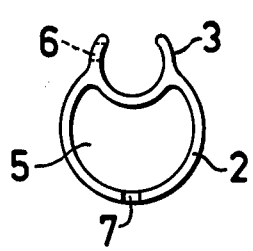
FIGS. 3, 4 and 5 are end, side and top views respectively of the embodiment shown in FIGS. 1 and 2.
Figure 4:
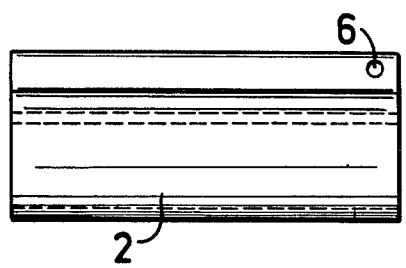
Figure 5:
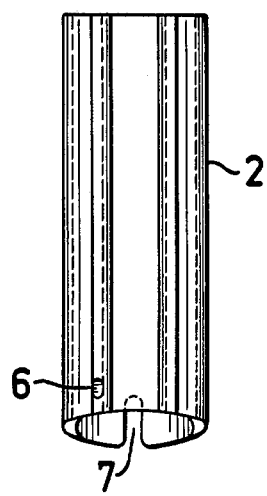
Figure 6:
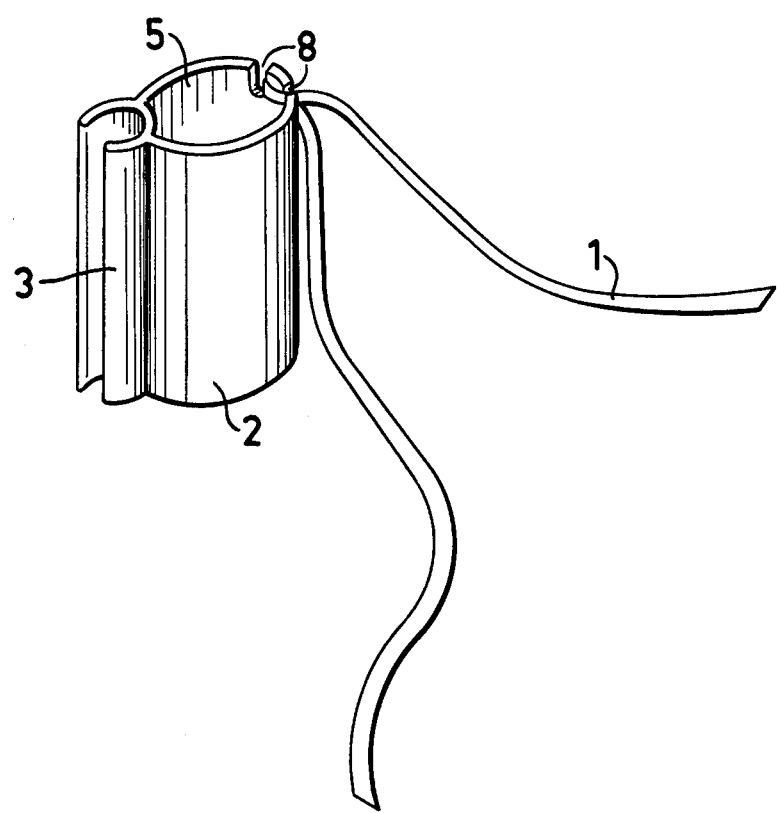
FIG. 6 is a perspective view of a second embodiment of my invention.
Figure 7:
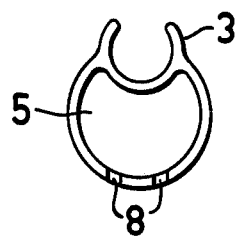
FIGS. 7, 8 and 9 are respectively end, side and top views of the second embodiment of my invention.
Figure 8:
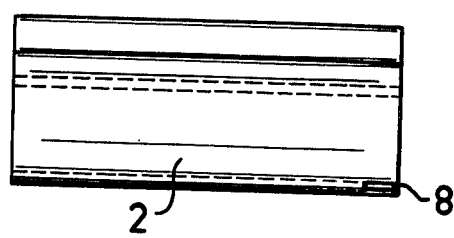
Figure 9:
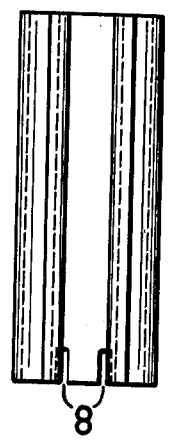

From FIGS. 3 and 7 it can be seen that the circle-area of the support-member 3 partly penetrates and intrudes on the circle-area of the teeth-shield member 2. This design is easily manufactured, but of course it is also possible that the circle-area of the support-tube 3 can lie totally inside or totally outside the circle-area of the teeth-shield member 2. For special applications it is also contemplated that several support members 3 could be arranged around the periphery of the teeth-shield member 2.

In the embodiment according to FIGS. 1 to 5 the support member 3 is at its top end provided with a hole 6 to which a band 1 is tied, preferably at the time of delivery to a hospital. In this embodiment the top portion of the teeth-shield member 2 has a bevelled end-surface with a groove 7 at the uppermost point, positioned diametrically opposite to the support-tube 3. The device according to this embodiment is suitably used in such a way that after insertion of the tube 4 in the support member 3 the tube 4 is tied to the support member 3 by use of the band 1, which has previously been attached to the hole 6. After achieving the desired positioning of the tube 4 and the teeth-shield member 2 in the mouth-cavity, for example with the tube at one corner of the mouth and with the teeth-shield two thirds inside the mouth and one third outside, the secured together tube 4 and teeth-shield member 2 are fixed in this desired position by tieing the remaining lengths of the band 1 around the neck of the patient in a desired manner. In this latter tieing one of the lengths of band 1 is positioned in the groove 7 whereby tube 4 and teeth-shield 2 can be more easily fixed side-by-side in the mouth-cavity. Such a tied up unit is effectively fixed in all directions. Neither tube nor teeth-shield can move sideways in the mouth, or in or out of the mouth or deeper down the throat. Nor can tube 4 or teeth-shield 2 internally or as a unit execute twisting or rotating movements. After use the unit can easily be removed by cutting the band 1, thus avoiding the disadvantages connected with the application and removal of smeary sticking-plaster.

In the embodiment according to FIGS. 6 to 9 the hole 6 in the support tube 3 is omitted. Instead, the top edge of the teeth-shield 2, which in this case can be straight (or unbeveled), is provided with two notches 8 in which the band 1 can be placed when fixing and tieing. This embodiment is used in the same way as the previous one except for the difference that when securing the tube, the band 1 is tied around the outside of the teeth-shield member and has the advantage of leaving the cavity 5 completely free from the band.

The material used in my device is suitably a thermoplastic, preferably polyvinylchloride or polyethylene. These materials are cheap and easily formable, have a suitable friction for effective fixation of the instrument and can easily be given any desired rigidity in order to function as a teeth-shield. My device can be manufactured in a number of ways. For example they can be made by injection moulding or fusing a thick tube together with a slit-open thinner tube). However, since the section shown in FIGS. 3 and 7 can very easily be extruded from plastic material, this inexpensive manufacturing method is preferred. After extrusion only cutting to length and the making of holes or notches for the band are needed. The teeth shield and the support member can also be formed separately and then joined together by an adhesive, thermal welding, etc.

The teeth shield member should have a circumference that is greater than either the tube 4 or the support member 3 and is formed so that it prevents direct biting of the instrument or tube 4. In its preferred form the teeth shield member 2 is in the form of a hollow cylindrical tube having a central cavity 5 through which additional instruments may be inserted. However, if desired the teeth shield member can be in the form of a solid tube without any central cavity.

In my device, the arrangement of the support member 3 at the periphery of the teeth shield member 2 insures that a tube inserted in the support member will become positioned at one corner of the patient's mouth so that space remains for access to the mouth-cavity with other instruments at the other corner of the patient's mouth or through the middle of the teeth-shield. In the latter case a channel is offered for fast and simple insertion of instruments without risk of contacting the patients teeth or by other contact hurt the patient. This possibility of inserting additional instruments is important, for example when an endotracheal-tube is inserted.

In conclusion, while the foregoing specification and drawings describe the construction, operation and use of two preferred embodiments of my invention, it is to be understood that I do not intend to limit myself to the precise constructions and arrangements herein disclosed, since the various details of construction, form and arrangement may obviously be varied to a considerable extent by anyone skilled in the art without really departing from the basic principles and novel teachings of this invention and without sacrificing any of the advantages of the invention and accordingly it is intended to encompass all changes, variations, modifications and equivalents falling within the scope of the appended claims.

I claim:

1. A device for protecting both a patient's teeth and a medical instrument when the medical instrument is to be inserted through the mouth of a patient, said device comprising in combination:
   (a) a tubular teeth shield member having a maximum internal diameter that is greater than the external diameter of said medical instrument,
   (b) a flexible instrument support member fixed to and extending along the exterior side of said tubular teeth shield member in a direction generally parallel to the longitudinal axis of said tubular teeth shield member, said instrument support member having a generally U-shaped configuration that opens outwardly so that it can receive and hold a medical instrument, and
   (c) band anchoring means on said device which is adapted to receive and hold a band, said band anchoring means consisting of at least one hole or one notch in members (a) and/or (b).

2. A device according to claim 1 wherein said anchoring means consists of at least one notch in the end of said tooth shield member.

3. A device according to claim 1 wherein said anchoring means consists of a hole in said instrument support member.

4. A device according to claim 1 which additionally includes securing means for securing said device to a patient.

5. A means according to claim 4 wherein said securing means is a band.

6. A device according to claim 1 wherein said teeth shield member includes a notch in one end that is located in opposed relationship to a hole in said instrument support member.

7. A device according to claim 1 wherein one end of said teeth shield member has two spaced apart notches therein.

8. A device according to claim 1 wherein a band is fixed to said band anchoring means.

9. A method for protecting a medical instrument when inserted through the mouth of a patient, as well as the patient, which method comprises the steps of
(1) attaching to the instrument a protecting device that comprises in combination
   (a) a tubular teeth shield member having a maximum internal diameter that is greater than the external diameter of said medical instrument,
   (b) a flexible instrument support member fixed to and extending along the exterior side of said tubular teeth shield member in a direction generally parallel to the longitudinal axis of said tubular teeth shield member, said instrument support member having a generally U-shaped configuration that opens outwardly so that it can receive and hold a medical instrument,
(2) displacing the device to position both the teeth shield and instrument support member between the teeth in the mouth cavity,
(3) rotating the device to orient the tubular teeth shield member and the instrument support member into a side-by-side position between the teeth, and
(4) securing the instrument to the instrument support member by means of a band after the attachment of the instrument to the device.

10. The method of claim 9 comprising the step of securing the device to the patient by means of a band.

11. The method of claim 10 comprising the step of using the band for both securing the instrument to the instrument support member and the device to the patient.